US012648711B2

(12) United States Patent
Imran et al.

(10) Patent No.: US 12,648,711 B2
(45) Date of Patent: Jun. 9, 2026

(54) SCREENING OF INDIVIDUALS FOR A RESPIRATORY DISEASE USING ARTIFICIAL INTELLIGENCE

(71) Applicants: Ali Imran, Bixby, OK (US); Iryna Posokhova, Kivsharivk (UA); Ali Rizwan, Lahore (PK)

(72) Inventors: Ali Imran, Bixby, OK (US); Iryna Posokhova, Kivsharivk (UA); Ali Rizwan, Lahore (PK)

(73) Assignee: AIFLYF LLC, Bixby, OK (US)

( * ) Notice: Subject to any disclaimer, the term of this patent is extended or adjusted under 35 U.S.C. 154(b) by 497 days.

(21) Appl. No.: 17/374,843

(22) Filed: Jul. 13, 2021

(65) Prior Publication Data

US 2021/0338103 A1 Nov. 4, 2021
US 2022/0104725 A9 Apr. 7, 2022

Related U.S. Application Data

(60) Provisional application No. 63/024,418, filed on May 13, 2020.

(51) Int. Cl.
*A61B 5/08* (2006.01)
*A61B 5/00* (2006.01)
(Continued)

(52) U.S. Cl.
CPC ........ *A61B 5/0823* (2013.01); *A61B 5/02055* (2013.01); *A61B 5/021* (2013.01);
(Continued)

(58) Field of Classification Search
CPC ... A61B 5/0823; A61B 5/7282; A61B 5/0002; A61B 5/7264; A61B 5/7267;
(Continued)

(56) References Cited

U.S. PATENT DOCUMENTS

2006/0198533 A1* 9/2006 Wang ....................... A61B 7/00
381/94.1
2007/0276278 A1* 11/2007 Coyle .................... A61B 5/369
600/301
(Continued)

OTHER PUBLICATIONS

Wang, Y, Wang, Y, Chen, Y, Qin, Q. Unique epidemiological and clinical features of the emerging 2019 novel coronavirus pneumonia (COVID-19) implicate special control measures. J Med Virol. 2020; 92: 568-576. https://doi.org/10.1002/jmv.25748 ( Year: 2020).*

*Primary Examiner* — Jennifer Robertson
*Assistant Examiner* — Elina Sohyun Jang
(74) *Attorney, Agent, or Firm* — Steven A. Nielsen; www.NielsenPatents.com

(57) ABSTRACT

An artificial intelligence-based system and method for scalable screening of individuals for respiratory infection, such as COVID-19. The system is trained to distinguish distinct latent features of cough sounds produced by a COVID-19 infected person from cough sounds produced by patients suffering from any other respiratory infection or involuntary cough sounds produced by a healthy person. Cough sound samples from individuals can be remotely collected and evaluated by the system for likelihood of the COVID-19 infection. Additionally, images of affected body parts, biomarkers, metadata, and other respiratory sound samples can also be used for screening.

17 Claims, 6 Drawing Sheets

(51) Int. Cl.

| | |
|---|---|
| *A61B 5/0205* | (2006.01) |
| *A61B 5/021* | (2006.01) |
| *A61B 5/024* | (2006.01) |
| *A61B 5/029* | (2006.01) |
| *A61B 7/00* | (2006.01) |
| *G16H 50/20* | (2018.01) |

(52) U.S. Cl.

CPC .......... *A61B 5/02405* (2013.01); *A61B 5/029* (2013.01); *A61B 5/0816* (2013.01); *A61B 5/082* (2013.01); *A61B 5/4011* (2013.01); *A61B 5/4017* (2013.01); *A61B 5/444* (2013.01); *A61B 5/4803* (2013.01); *A61B 5/4824* (2013.01); *A61B 5/7267* (2013.01); *A61B 5/7275* (2013.01); *A61B 5/742* (2013.01); *A61B 7/003* (2013.01); *G16H 50/20* (2018.01)

(58) Field of Classification Search

CPC ..... A61B 5/0816; A61B 5/7275; A61B 7/003; A61B 5/742; A61B 2562/0204; A61B 5/0077; A61B 5/02055; A61B 5/02405; A61B 5/029; A61B 5/082; A61B 5/14542; A61B 5/318; A61B 5/4011; A61B 5/4017; A61B 5/444; A61B 5/4803; A61B 5/4824; A61B 5/681; A61B 5/746; A61B 5/021; G16H 50/20; G16H 50/80; Y02A 90/10

See application file for complete search history.

(56)                References Cited

U.S. PATENT DOCUMENTS

| | | | |
|---|---|---|---|
| 2010/0070268 A1* | 3/2010 | Sung ........................ | G10L 15/24 704/226 |
| 2011/0093249 A1* | 4/2011 | Holmes .................. | G16H 50/50 703/6 |
| 2015/0073306 A1* | 3/2015 | Abeyratne ............. | G16H 50/30 600/586 |
| 2020/0152330 A1* | 5/2020 | Anushiravani .......... | A61B 5/11 |
| 2020/0160881 A1* | 5/2020 | Gadgil ..................... | G06N 3/08 |
| 2020/0245873 A1* | 8/2020 | Frank .................. | A61B 5/0823 |
| 2020/0381130 A1* | 12/2020 | Edwards ................ | G10L 15/16 |
| 2021/0076977 A1* | 3/2021 | Abeyratne ........... | A61B 5/7267 |

* cited by examiner

SCREENING OF INDIVIDUALS FOR A RESPIRATORY DISEASE USING ARTIFICIAL INTELLIGENCE

CROSS-REFERENCE TO RELATED APPLICATIONS

This application claims priority from the U.S. provisional patent application Ser. No. 63/024,418, filed on May 13, 2020, which is incorporated herein by reference in its entirety.

FIELD OF INVENTION

The present invention relates to artificial intelligence-based screening of individuals for respiratory disease, and more particularly, the present invention relates to an artificial intelligence-based screening of individuals for a respiratory disease using cough sound acoustics.

BACKGROUND

Epidemic refers to an unexpected increase in the number of disease cases in a specific geographical area. An epidemic is said to occur in an area when an infectious disease becomes prevalent in the area. The term epidemic is interchangeably used with the term outbreak which refers to a sudden spike in the number of cases of the same infectious disease in an area. When an epidemic spread to several countries, it is referred to as a pandemic. Pandemics are known to have caused unprecedented loss of human life. The influenza pandemic caused by virus HIN1 in 1918 is considered the deadliest outbreak of the twentieth century. COVID-19 pandemic has been a disaster for the 21st century that has affected almost the entire planet and caused millions of deaths.

The infectious agents responsible for an epidemic rapidly spreads from one person to another through contact and air. In the beginning, the spread is from one person to another followed by one person to many, and then at peak, the infection spreads in clusters. Quarantine of infected persons has been undoubtedly found to be an effective strategy to decelerate the spread of infections. However, early diagnosis of disease through rapid testing of the population is essential for an effective strategy against the spread of the disease.

Inability to test and monitor at scale has been Achille's heel in humanity's war against the pandemics such as COVID-19. Existing diagnostic methods for such infections are costly and time taking. Moreover, the testing requires a person to visit a lab or send the test medium such as nasopharyngeal or oropharyngeal swab to the lab. Lack of medical facilities, particularly in developing countries slows down the testing drive. Moreover, the cost of diagnostic kits can also be a deterrent in developing countries. By the time a person gets tested and receive a report, he may become symptomatic and may have already passed the infections unknowingly to many.

Thus, a long-term desire is there for an effective solution for a scalable screening or diagnosis method that can enable continual in-situ or remote screening at scale.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a system and method for screening individuals for respiratory disease.

It is another object of the present invention that the screening can be quickly and easily implemented at a large scale.

It is still another object of the present invention that the screening can be done remotely.

It is yet another object of the present invention that screening can be cost-effective.

It is a further object of the present invention that a result of the screening can be published quickly in few minutes.

It is still a further object of the present invention that the system and method can provide for population-level continual screening.

It is yet a further object of the present invention that the system and method can provide for spatiotemporal monitoring of the spread and predict future hotspots/clusters of infections.

It is an additional object of the present invention that the system and method can provide a scalable solution for very early detection of pandemics such as COVID-19.

It is still an additional object of the present invention that the system and method can assist government and healthcare agencies in planning and execution of strategies against the spread of infection.

It is yet an additional object of the present invention that the system and method can reduce unnecessary exposure of medical staff and load on clinical testing and care facilities.

It is an object of the present invention that the system and method can provide for hotspot breakout prediction with community-level resolution without compromising privacy.

In one aspect, disclosed is a system and method for scalable screening of individuals for respiratory infection, such as COVID-19. The disclosed system and method can use respiratory sounds including the sound of voluntary or involuntary coughing recordable from ubiquitously available devices such as phones as an essential input. As additional optional input for higher specificity, the invention can also use skin images, biomarkers, and subject's metadata such as medical history as an optional input. The input can be processed by a novel AI engine implemented within the disclosed system and returns the screening results instantly to the individual. The solution can be deployable remotely or in-situ, anytime, anywhere via phones, smartphones, wearable devices such as smartwatches or other custom wearable devices or ambient sensors, and audio/video/image recording devices.

In one aspect, the disclosed system and method can receive locations of individuals and the location of the individuals with their screening result can be used to determine the rate and pattern of the spread of the infection. The disclosed system and method using the AI engine can then predict the next hotspot or cluster spread of infection using the near real-time rate and pattern of the spread.

In one aspect disclosed is a method for predicting a likelihood of having a respiratory infection in an individual, the method implemented within a screening system, the screening system has a processor and a memory, the method includes the steps of: receiving, by the screening system, cough samples from subjects suffering from the respiratory infection and subjects not suffering from the respiratory infection; pre-processing the cough samples, by a pre-processing module implemented within the screening system, into labeled features obtaining a training dataset; randomly partitioning the training dataset into a plurality of training datasets; generating a plurality of classifiers, by the screening system using machine learning, based on the plurality of training datasets, wherein at least one classifier of the plurality of classifiers is a deep learning classifier; and assigning a weightage, by the screening system, to each classifier of the plurality of classifiers.

In one implementation of the method for predicting a likelihood of having a respiratory infection in an individual, the method further includes the steps of: receiving, by the screening system, a sound sample from an individual, the sound sample includes a cough sound; pre-processing the sound sample, by the pre-processing module, to remove noise and extract a set of unique latent features; processing the set of unique latent features by each of the plurality of classifiers to obtain a plurality of outputs, each output of the plurality of outputs indicates a likelihood of having the respiratory infection or not having the respiratory disease; computing, by a mediator module implemented within the system, an average weightage of the plurality of outputs based on the weightage assigned to each classifier of the plurality of classifiers to obtain a result, wherein the result classifies the individual into a category indicative of a likelihood of having the respiratory infection or into another category indicative of a likelihood of not having the respiratory infection; and communicating, by the mediator module, the result to the individual.

In one implementation of the method for predicting a likelihood of having a respiratory infection in an individual, the method further includes the steps of: configuring, the pre-processing module and the plurality of classifiers into an individual device; receiving a sound sample from an individual through a microphone coupled to the individual device, the sound sample includes a cough sound; pre-processing the sound sample, by the pre-processing module, to remove noise and extract a set of unique latent features; processing the set of unique latent features by each of the plurality of classifiers to obtain a plurality of outputs, each output of the plurality of outputs indicates a likelihood of having the respiratory infection or not having the respiratory infection; computing, by the individual device, an average weightage of the plurality of outputs based on the weightage assigned to each classifier of the plurality of classifiers to obtain a result, wherein the result classifies the individual into a category indicative of a likelihood of having the respiratory infection or into another category indicative of a likelihood of not having the respiratory infection; and presenting the result on a display coupled to the individual device.

In one implementation of the method for predicting a likelihood of having a respiratory infection in an individual, the respiratory infection is COVID-19 infection.

In one implementation of the method for predicting a likelihood of having a respiratory infection in an individual, the method further includes the steps of: computing a plurality of results for a plurality of individuals; receiving a plurality of location coordinates of the plurality of individuals; and applying machine learning algorithms to the plurality of individuals and the plurality of location coordinates for presenting in near real time rate and pattern of a spread of the respiratory infection. The method may further include the steps of predicting, by the screening system, cluster spreads of the respiratory infection in near future. The method further includes the steps of receiving past mobility patterns, from an external server, of the plurality of individuals, wherein the predicting of the cluster spreads is further based upon the past mobility patterns.

In one implementation of the method for predicting a likelihood of having a respiratory infection in an individual, the method further includes the steps of: receiving, by the screening system, a plurality of parameters selected from a group consisting of biomarkers, metadata, neurologic manifestations including central nervous system manifestations and peripheral nervous system manifestations, and image(s) of cutaneous manifestations of the respiratory infection in a form of anomalies in skin; and pre-processing the plurality of parameters to obtain a plurality of additional training datasets, wherein the generating of the plurality of classifiers is further based on the plurality of additional training datasets. The biomarkers are selected from a group consisting of respiration rate, body temperature, blood oxygen saturation, pulse rate, heart rate variability, resting heart rate, blood pressure, mean arterial pressure, stroke volume, sweat level, systematic vesicular resistance, cardiac output, pulse pressure, cardiac index, one lead ECG, and breath chemical composition including volatile organic compounds. The metadata is selected from a group consisting of age, gender, smoking, non-smoking, ethnicity, and medical history. The central nervous system manifestations are selected from a group consisting of dizziness, headache, impaired consciousness, acute cerebrovascular disease, ataxia, and seizure, and the peripheral nervous system manifestations are selected from a group consisting of taste impairment, smell impairment, vision impairment, and nerve pain. Provided that wherein the step of assigning the weightage to each classifier is further based on a parameter of the plurality of parameters used for generating each classifier.

In one aspect, disclosed is a method for predicting a likelihood of having a respiratory infection in an individual, the method implemented within a screening system, the screening system has a processor and a memory, the method includes the steps of: receiving, by the screening system, a sound sample from an individual, the sound sample includes a cough sound; pre-processing the sound sample, by a pre-processing module, to remove noise and amplification, the pre-processing module implemented within the screening system; applying a deep learning-based classifier to detect cough sound in the sound sample; applying a feature extraction algorithm to the sound sample to extract a set of unique latent features; and processing the set of unique latent features by one or more machine learning based classifiers to classify the individual into a category indicative of a likelihood of having the respiratory infection or into another category indicative of a likelihood of not having the respiratory infection. In one case, the respiratory infection can be COVID-19 infection. The sound sample can further include nasal breathing sounds and vocalization sounds. The one or more machine learning based classifiers can include a deep transfer learning-based binary classifier.

These and other objects and advantages of the embodiments herein and the summary will become readily apparent from the following detailed description taken in conjunction with the accompanying drawings.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
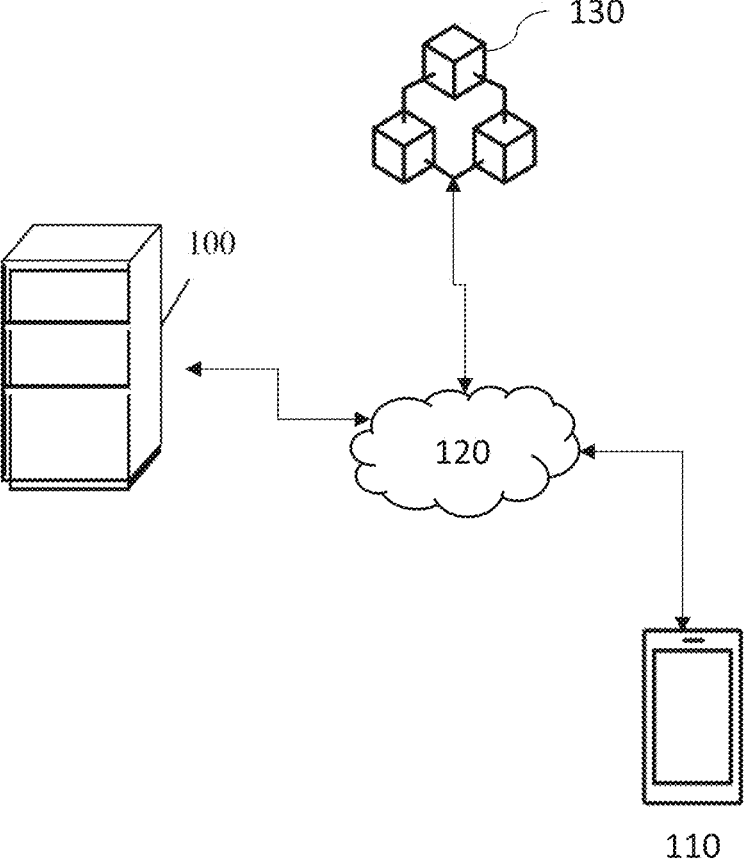
FIG. 1 is an environmental diagram showing the disclosed system in communication with an individual device and external servers, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a scalable solution for screening a respiratory disease, such as COVID-19 for anyone, anytime, and anywhere. Respiratory disease can be caused by pathogenic bacteria and viruses. In particular, the viral infections that chiefly affect the respiratory system and can rapidly spread from one person to another can be tele-screened by the disclosed system and method. The disclosed system and method can also provide for COVID-19 monitoring at the population level by providing live maps of the spatiotemporal spread, risk of exposure prediction and alerting for individuals, and future hotspot prediction.

It was established by suitable studies that the different respiratory infections differently effect the respiratory system. The pathomorphological changes in the respiratory system affects the sounds produced including cough sounds, breathing sounds, and vocalization. Different pathomorphological changes caused by different infectious agents also affect the sounds differently. For example, in a study to investigate distinctness of pathomorphological alterations in the respiratory system induced by COVID-19 infection when compared to other respiratory infections, cough sound data of from COVID-19 infected patients and patients infected form other respiratory infections including pertussis and bronchitis were collected. Cough sound samples from COVID-19 patients include both spontaneous cough (symptomatic) and non-spontaneous (i.e., when the patient is asked to cough). This is to make the test applicable to those who may not be showing cough as a symptom yet but are already infected. Cough samples were also collected from otherwise healthy individuals with no known medical condition, hereafter referred to as a normal cough. The normal cough was included in the analysis to see if it can be differentiated from the simulated cough produced by the COVID-19 patients. The collected data was pre-processed and analyzed using a variety of data analysis and pre-processing tools. Multiple alternative analysis approaches showed that COVID-19 associated cough has certain distinct features. Moreover, the distinctness of pathomorphological changes caused by COVID-19 in the respiratory system was established by examining the X-rays and CT scans of COVID-19 patients. COVID-19 related pneumonia was also found to have distinct pathomorphological alternations in respiratory system compared to normal bacterial pneumonia.

In COVID-19 infection, starting from day two of the exposure, the infection starts inducing pathomorphological, physiological, pathological, cutaneous, and psychological alternations in the human body. This disclosed artificial intelligence-based system and method can use the subtle distinctness of the COVID-19 induced pathomorphological (particularly in the respiratory system), physiological, pathological, cutaneous, and psychological alternations in the human body to determine the likelihood of COVID-19 infection in an individual at a very early stage. The AI-diagnostic engine of the disclosed system can use the cough sound samples from subjects to determine the likelihood of respiratory infections including the COVID-19 infection. The coughing sound can be spontaneous (involuntary) or can be simulated (voluntary) by the test subject. Besides the cough sound samples, other respiratory sounds can also be used such as the respiratory sounds affected by the pathological conditions of the respiratory system. For example, breathing sounds, vocalizations of pre-defined words and/or sentences can be used to gauge lung capacity and breathing difficulty.

Apart from respiratory sounds, the disclosed system can also use other body parameters as an input in the underlying diagnosis of a disease condition or to increase the accuracy of screening of individuals for COVID-19 infection and similar respiratory diseases. In one case, images of affected body portions can be taken using the camera attached to an individual device. This includes pictures/videos of the face, hands, and feet, and retina. Biomarkers, such as respiration rate, body temperature, blood oxygen saturation, pulse rate, heart rate variability, resting heart rate, blood pressure, mean arterial pressure, stroke volume, sweat level, systematic vesicular resistance, cardiac output, pulse pressure, cardiac index, one lead ECG, breath chemical composition including volatile organic compounds, and like body parameters that are known to a skilled person for the diagnosis of pathophysiological conditions in humans can also be used. Metadata, such as age, gender, smoking, non-smoking, ethnicity, medical history, and like information can also be taken from an individual. The choice of biomarkers may depend on the availability of the collection methods. The disclosed system can work with all variants of data collection methods. For example, the essential input data can be collected via a phone (e.g., via a call), a smartphone or similar device such as a tablet, laptop, or computer, or any custom device such as a smartwatch, wristband, necklace, or ring that has sound recording capability. The optional data can be collected via a wearable device such as a smartwatch, wrist band, necklace, earbuds, a ring, or simply a skin patch over the skin or a chip planted under the skin. The optional data can also be collected with a custom device that can operate on its own or in conjunction with a smart device such as a smartphone, Alexa, etc. Both essential and optional data can also be collected from combinations of ambient sensors such as CCTV cameras, infrared cameras, sound recording devices such as Alexa, Google Home, or a combination of devices and sensors carried on the person or embedded in the environment. It is to be understood that the disclosed system can use cough sound samples to detect the likelihood of COVID-19 infection, other information like age, gender, smoking, body temperature, other respiratory sounds, can be used to increase the confidence level of the screening results.

The disclosed system can process the collected data to extract, augment and amplify latent features in collected data linked with COVID-19 infection. These features include, but are not limited to, distinct latent features in cough sound associated with COVID-19 induced pathomorphological alternations in the respiratory system; cutaneous manifestations of COVID-9 infection in form of anomalies in skin; anomalies in one or more of the following biomarkers: respiration rate, temperature, blood oxygen saturation, pulse rate, heart rate variability, resting heart rate, blood pressure, mean arterial pressure, stroke volume, sweat level, systematic vesicular resistance, cardiac output, pulse pressure, cardiac index, one lead ECG and breath chemical composition including volatile organic compounds; and neurologic manifestations that included but are not limited to central nervous system manifestations (dizziness, headache, impaired consciousness, acute cerebrovascular disease, ataxia, and seizure), peripheral nervous system manifestations (taste impairment, smell impairment, vision impairment, and nerve pain), and skeletal muscular injury manifestations.

The extracted features can then be passed on to a multi-pronged AI engine implemented within the disclosed system that can return the likelihood of the presence of COVID-19.

Besides screening of an individual for COVID-19 infection, the disclosed system can also provide for COVID-19 monitoring and predictive analysis including individual risk and future hotspot/outbreak prediction solutions. The disclosed system may also allow spatiotemporal monitoring and prediction of the COVID-19 spread. This system can take the screening results of individuals for COVID-19 infection and fuses them with the location information and/or mobility pattern of the tested and/or untested mobile network users. The location information can come from the individual device or the telecom network. Mobility patterns may come from the past call detailed record data or Handover traces of the individual devices. The analysis can be graphically presented as an overlay on a dynamic map showing continuous near real time spread of infection. The predicted future hotspots/cluster spread of infection can also be graphically presented.

Now referring to FIG. 1, which shows an environmental diagram showing the disclosed system 100 that can be connected to an individual device 110 and an external server 130 through a network 120. The individual device can be a keypad phone, smartphone, laptop, desktop, tablet computer, personal digital assistant ("PDA"), smartwatches, and like. In brief, the individual device can be any device with a microphone to record sound and network connectivity for sending the audio file over a network. The individual device can also include an operating system, such as but not limited to Android, iOS, Windows, macOS, blackberry, and Linux. The individual device can have a physical input interface, such as a keypad or touch screen for receiving an input and a display to view instructions received from the system and presenting the screening results. The individual device can also include a network circuitry for connecting to a network 120. The network can be wired or wireless network. The wired network may include DSL and optical fiber lines. The wireless network may include Bluetooth®, Wi-Fi, WiMAX, and cellular networks including GPRS, LTE, CDMA, 3G, 4G, and 5G. The network can be a secure network or an unsecured network. The disclosed system 100 can also be connected to an external server 130 for covid-19 tracking and hotspot predictions. FIG. 1 shows the individual device and the external servers connected through the same network for illustration purposes only, however, it is to be understood that the different individual devices can connect simultaneously to the disclosed system through different networks and using different network communication protocols. Moreover, the same individual device can connect with the disclosed system 100 through more than one network.

Figure 2:
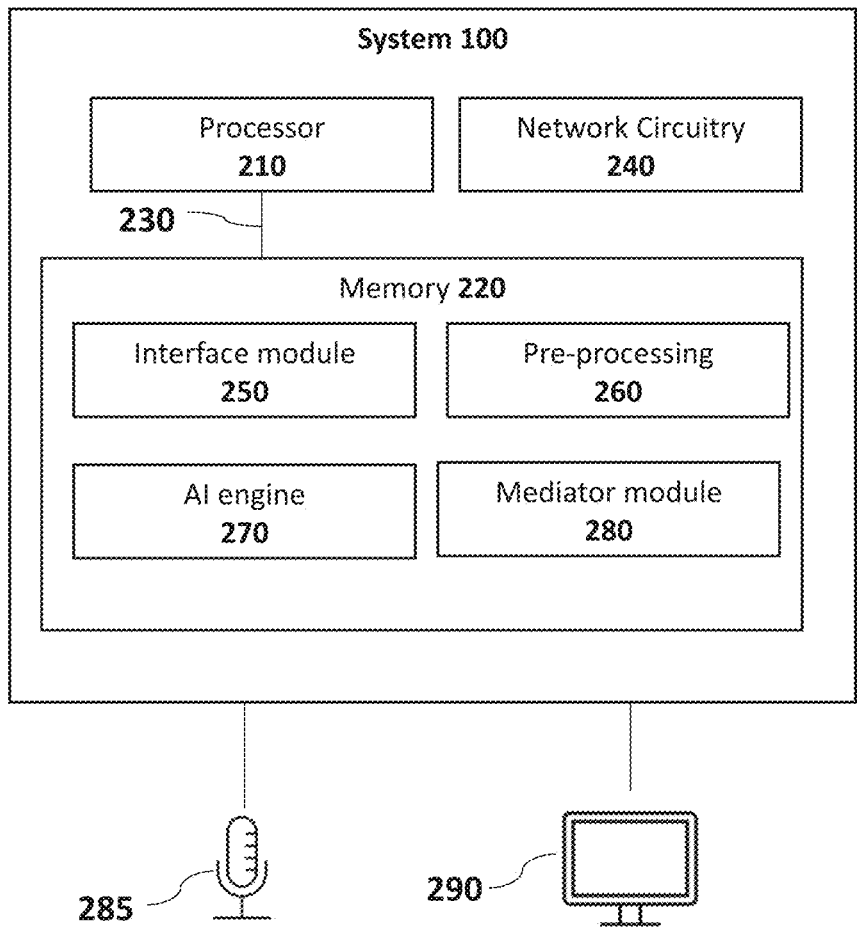
FIG. 2 shows the system architecture, according to an exemplary embodiment of the present invention.

Referring to FIG. 2 which is a block diagram showing the architecture of the disclosed system 100 for screening individual devices for respiratory disease. The system 100 can include a processor 210 coupled to a memory 220 through a system bus 230. The system 100 may also include a network circuitry 240 coupled to the processor through the system bus 230 for connecting the system 100 to an external network. The processor 210 can be any logic circuitry that responds to and processes instructions fetched from the memory 220. Suitable examples of the processors commercially available include the processors available from Intel, AMD, Snapdragon, Exynos, MediaTek, Apple, and like. The memory 220 may include one or more memory chips capable of storing data and allowing any storage location to be directly accessed by the processor 210. As shown in FIG. 2, the memory can include modules according to the present invention for execution by the processor 210 to perform one or more steps of the disclosed computer-implemented method for the screening of individuals for a respiratory disease. Memory 220 can include an interface module 250, a pre-processing module 260, an AI engine 270, and a mediator module 280. It is to be understood that all the modules are shown implemented within the disclosed system, however, a skilled person will appreciate that one or more module can also be implemented within an individual device having a processor and a memory or one or more steps of the disclosed computer implemented may also be performed one the individual device.

The interface module 250 upon execution by the process can provide an interface on the individual device 110. The interface can be provided as application software that can be installed on the individual device 110. The application software can be developed for Android™, iOS, Chrome, and any other known operating platform for mobile devices. The application software can be made available through a distribution service provider, for example, Google Play™ operated and developed by Google, and the app store by Apple. In addition to the application software, a website-based interface can also be provided through the world-wide-web. The application software can also be provided for the desktop environment, such as Windows™, Linux, and macOS. The interface may permit interacting with an individual through the individual device, wherein information can be presented on the individual device by the system 100 and information can be received by the system 100 from the individual device. Moreover, the interface may allow the individual to upload audio and images. The interface may provide step-by-step instruction and/or demo to the individual to record cough and other respiratory sounds. Moreover, the interface may also provide for capturing images of the face, hands, and any other affected body part relevant as input for the screening of the infection. The interface may also request information through a form presented within the interface, the information can include contact details, age, gender, smoking habits, previous illnesses, and like. The disclosed system 100 can also be connected to a microphone 285 for capturing audio from an individual and a display 290.

The recorded audio sample can be received by the pre-processing module 260. The pre-processing module 260 upon execution by the processor can provide for noise cancellation, amplification, feature extraction, and verification of the sound samples. In case, the sound samples do not have a cough sound, or the quality of the cough sound is poor, the pre-processing module can reject the sound sample. The AI engine 270, upon execution by the processor, can distinguish between a COVID-19 cough and any different cough or no cough. The AI engine can include one or more machine learning based classification algorithms, such as a deep Transfer Learning-based Binary Class classifier, Deep Transfer Learning-based Multi Class classifier, and Classical Machine Learning based Multi Class classifier. The memory can also include a mediator module 280 which upon execution by the processor, can evaluate the findings of the different classifiers of the AI engine based on the predetermined weightage assigned to each classifier to determine the screening result. The mediator module 280 may take into account the accuracy, confidence, amount of training data and reliability of the architecture of each classifier to assign a weight to each classifier and takes weighted average of the outcome of each classifier to determine the final result and return it to the user. The outcome of each classifier can indicate the likelihood of having the respiratory infection or not having the respiratory infection. The outcome of the screening i.e., the screening results presented to the user can be COVID-19 infection likely, COVID-19 not likely or the Test inconclusive. However, any outer output format is within the scope of the present invention. For example, the screening resulting can just present positive and negative.

Figure 3:
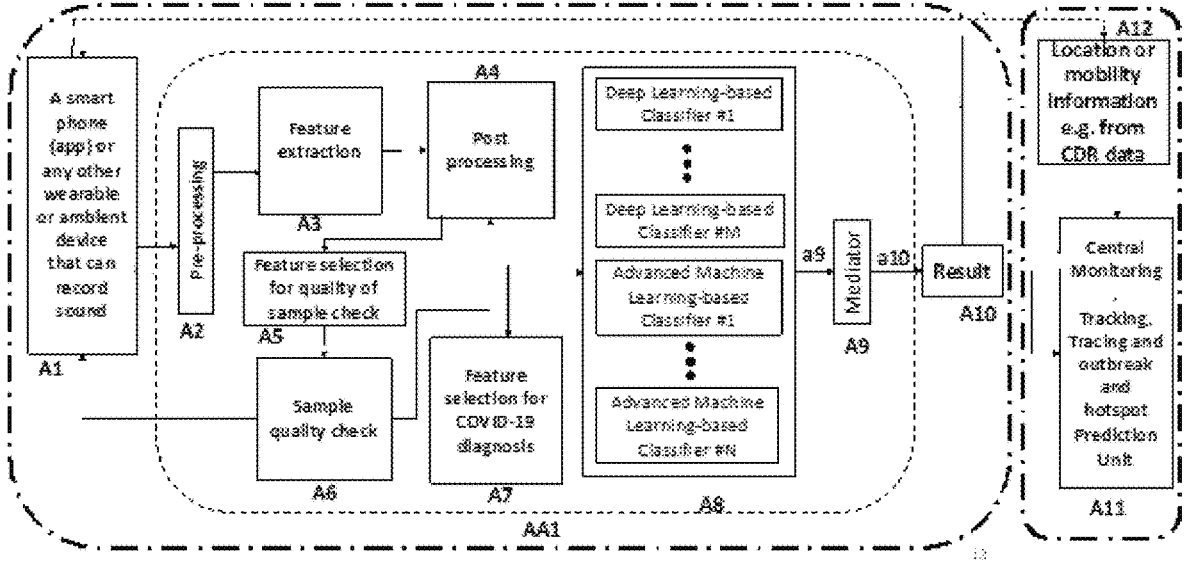
FIG. 3 is a block diagram showing an exemplary embodiment of the method for screening individuals for COVID-19 infection using cough and respiratory sounds, according to an exemplary embodiment of the present invention.

Referring to FIG. 3, which is a block diagram showing an exemplary embodiment of the computer-implanted method implemented by the disclosed system 100 for screening an individual for COVID-19 infection. Block A1 can receive cough sound samples and other respiratory sounds from an individual through the individual device. The individual can be instructed by the system if how to record the cough sound. In case, the individual does not have a cough, the system can instruct the individual to simulate the cough. The cough sounds can be received through a mobile device of a user. For example, the cough sounds can be received on an audio call. Alternatively, the cough sounds can be received through an interface provided on the individual device by the interface module 250, wherein the interface can show stepwise instruction with any visual demonstration for recording the cough sounds voluntary or involuntary. Besides the cough sound, any other respiratory sound can also be recorded by the user based on the instructions provided by the disclosed system. The user can be provided with a demonstration either through audio or graphics or both to produce the respiratory sounds. For example, a list of words and/or sentences can be displayed on the user interface which the user can speak in the microphone. The user can also repeat the sounds demonstrated by the disclosed system. Optionally, breathing sounds can also be collected from the user, wherein the microphone can be placed near the nose for nasal breathing sounds and tracheal breath sounds by placing the microphone on the parapharyngeal space. Block A2 in FIG. 3 can receive the sound sample from the individual device for verification and pre-processing. A2 can provide for background noise removal from the audio sample. This can make the screening test useful even at public places such as airports, train or bus terminals, support events, or crowded shopping malls.

The artificial intelligence-based pre-processing at A2 can minimize the effects of different types of noise present in the sound data, such as background noise when a person is coughing, or the noise introduced by the microphone itself. It may be important to offset any random noises so that the AI engine can learn the latent distinguishable features present in the cough sound samples rather than overfitting these random noises. Different temporal and spectral pre-processing techniques can be leveraged such as amplitude normalization, audio segmentation, frequency-selective filtering, and pitch shifting for removal of noise in samples. Amplitude normalization to ensure that the peak amplitude/loudness in all audio samples is normalized. Cough audio segmentation extracts the useful temporal segments in the input audio sample by finding the start and end of the cough auditory scenes, such as energy-based segmentation. Filtering helps in filtering out the important spectral portion of the input audio signal by leveraging low-pass or band-pass filters. The pitch shifting (or scaling) process creates augmented data by raising and lowering the audio pitch in the initial training data. A2 can perform the data formatting to conform the recorded sound as the same format e.g., by doing clipping and time-shifting. A3 can provide for features extraction from the audio samples using a feature extraction algorithm that can extract over three hundred features from the recorded sound. Representative examples of such features are listed in below Table 1.

TABLE 1

Features extracted from an audio sample including cough sound.

| ID | Feature Name | Description |
|---|---|---|
| 1 | Zero Crossing Rate | The rate of sign-changes of the signal during the duration of a particular frame. |
| 2 | Energy | The sum of squares of the signal values, normalized by the respective frame length. |
| 3 | Entropy of Energy | The entropy of sub-frames' normalized energies. It can be interpreted as a measure of abrupt changes. |
| 4 | Log Energy | The log energy for every subsegment |
| 5 | Skew | skewness is a measure of the asymmetry of the probability distribution of the data segment |
| 6 | Kurtosis | kurtosis is a measure of the "tailedness" of the probability distribution of the data segment |
| 7 | Spectral Centroid | The center of gravity of the spectrum. Approximately related to timbral "brightness |
| 8 | Spectral Mean | $1^{st}$ spectral moment |
| 9 | Spectral Variance | $2^{nd}$ spectral moment |
| 10 | Spectral Kurtosis | $4^{th}$ spectral moment |
| 11 | Spectral Skewness | $3^{rd}$ spectral moment |
| 12 | Spectral Spread (SSp) | Variance of the spectrum around the spectral centroid |
| 13 | Spectral Slope (SSl) | measure of how quickly the spectrum of an audio sound tails off towards the high frequencies |
| 14 | Spectral Crest Factor | Ratio of the maximum of the spectrum to the sum of the spectrum |
| 15 | Spectral Bandwidth | measure of the spectral dispersion |
| 16 | Spectral Flatness | Ratio between geometric and arithmetic means |
| 17 | Spectral Spread | The second central moment of the spectrum. |
| 18 | Spectral Entropy | Entropy of the normalized spectral energies for a set of sub-frames. |
| 19 | Spectral Flux | The squared difference between the normalized magnitudes of the spectra of the two successive frames. |
| 20 | Bispectrum Score (BGS) | 3rd order spectrum of the signal is known as the bispectrum. |
| 21 | Pitch | The fundamental frequency of the audio signal |
| 22 | MaxF | Maximum Frequency |
| 23 | Band Power | average power in the input signa |
| 24 | Spectral Rolloff | The frequency below which 90% of the magnitude distribution of the spectrum (spectrum's energy) is concentrated. |
| 25 | Spectral Turbulence | Quantifies variations over time in the spectral content |
| 26-45 | Mel-Spectrogram | Mel-freuency spectrogram coefficients for 20 Mel-bands |
| 46-58 | MFCCs | Mel Frequency Cepstral Coefficients form a cepstral representation where the frequency bands are not linear but distributed according to the mel-scale. |
| 59-71 | Delta MFCCs | Delta-MFCC and Delta-Delta-MFCC are used to extract the features of speakers. |
| 72-84 | Delta Delta MFCCs | Deita-MFCC and Delta-Delta-MFCC are used to extract the features of speakers. |
| 85-96 | Chromagram | A 12-element representation of the spectral energy where the bins represent the 12 equal-tempered pitch classes of western-type music (semitone spacing). |
| 97 | Chroma Deviation | The standard deviation of the 12 chroma coefficients. |
| 98-109 | Constant-Q chromagram | Constant Q, transform based Chroma Values |
| 110-121 | Chroma Energy Normalized Statistics | Chroma Energy Normalized variant of Chroma values |
| 122-141 | Cochleagram | Gamma-tone filter based variant of spectrogram |
| 142-161 | Linear Predictive Coefficients (LPC) | Spectral envelope of a digital signal of speech in compressed form |
| 162-181 | Linear Predictive Cepstral Coefficients (LPCC) | Cepstral coefficients derived from LPC calculated spectral envelope |
| 182-201 | Line Spectrum Pairs (LSP) | Direct mathematical representation of LPC coefficients for added filter stability and efficiency |
| 202-221 | Discrete wavelet transform (DWT) | decomposes a signal into a group of basic functions called wavelets |
| 222-241 | Continuous Wavelet Transform (CWT) | provides an overcomplete representation of a signal by letting the translation and scale parameter of the wavelets vary continuously |
| 242-261 | Perceptual linear prediction (PLP) | perceptual linear prediction coefficients |
| 262-265 | Formant Frequencies (FF) | A formant is the spectral shaping that results from an acoustic resonance of the human vocal tract. |
| 266 | Non-gaussianity score (NGS) | NGS gives the measure of non-gaussianity of a given segment of data. |
| 267-286 | Power Spectral Density (PSD) | A Power Spectral Density (PSD) is the measure of signal's power content versus frequency. |
| 287-292 | Tonnetz | Tonal centroid features (tonnetz) |

TABLE 1-continued

Features extracted from an audio sample including cough sound.

| ID | Feature Name | Description |
|---|---|---|
| 293-299 | Spectral Contrast | spectral peak, the spectral valley, and their difference in each frequency subband |
| 300-312 | Local Hu Moments | Measure the degree of how the energy is concentrated to the center of energy gravity of local region of spectrogram |

The feature extraction algorithm can be configured based on audio acoustics and medical domain knowledge. Additionally, automated feature extraction methods such as auto-variational encoders and principal component analysis can also be used. A4 in junction with A5 and A7 can determine the variants, sub-components, and combinations of the features, using domain knowledge, to be fed to A6 and A8 respectively. A5 and A7 blocks can use multi-dimensional scaling to maximize the entropy and reduce the dimensions of the input feature vectors to the later blocks.

Figure 4:
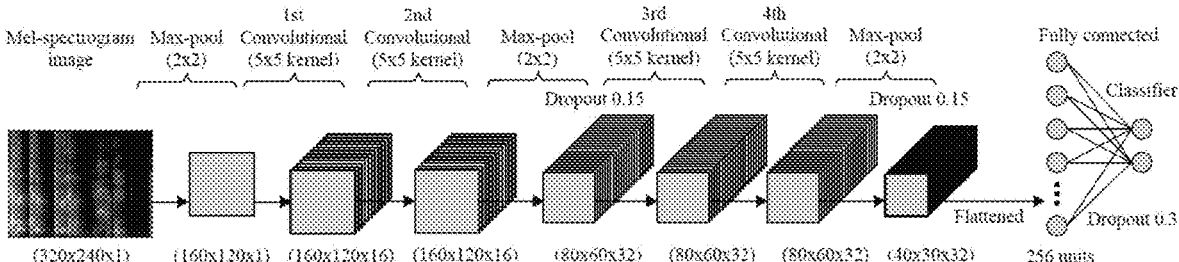
FIG. 4 shows an example of a deep learning-based classifier used for cough detection, according to an exemplary embodiment of the present invention.
Figure 5:
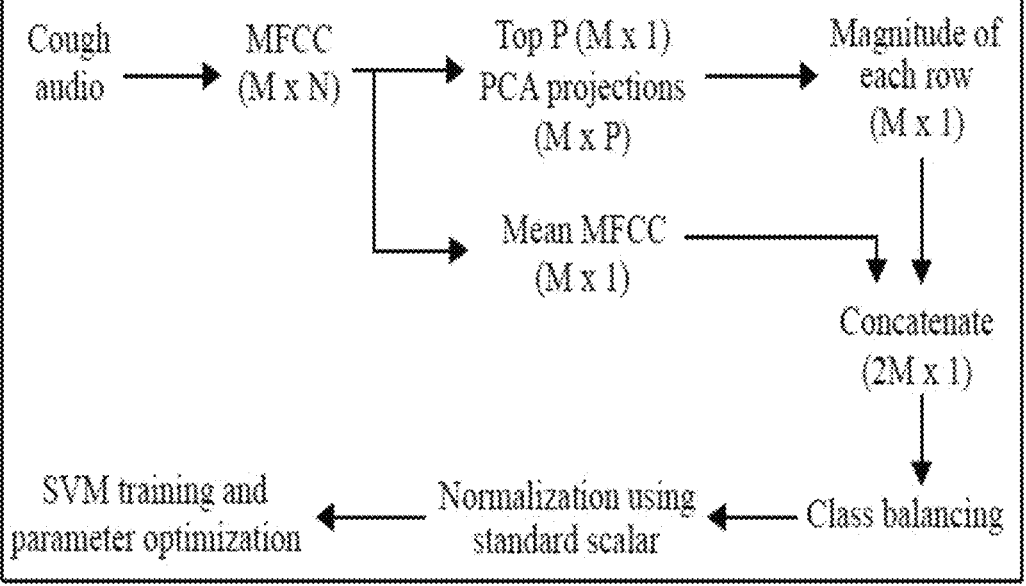
FIG. 5 shows an example of a deep learning-based classifier, according to an exemplary embodiment of the present invention.

A6 can perform quality assurance to ensure the input audio has the core sounds needed to perform the diagnosis. For example, A6 determines if the input sound includes sufficient duration of cough sounds. A6 essentially consists of deep learning and non-deep learning-based classifiers. FIG. 4 presents an example of a deep learning-based classifier used in an exemplary embodiment for the cough detection part (A6). These classifiers take the input and classify it as acceptable or non-acceptable for being passed on to the diagnosis engine in A8. If the recorded input audio sample does not meet the qualifications for being used for the screening, A6 prompts the recording device via an interface to indicate the same to the individuals. If the recorded input audio meets the quality threshold e.g., it has the sufficient amount of cough sound and other sounds needed for the diagnostic value, it prompts the A4. A4 in turn then passes on the select features of this particular input to A7. A7 receives variants, sub-components, and combinations of the sound features identified in Table 1 from A4 and perform algebraic operations and transformations on these features to make them suitable to be fed to the diagnostic AI engine core part A8. A8 can include multiple multi-class as well as binary classifiers. Some of these classifiers are based on deep learning and use convolutional neural networks as well as other variants of deep neural networks. FIG. 5 presents an example of a deep learning-based classifier used in a prototype embodiment for the cough detection part (A6). This figure just explains the principle, the actual embodiment in A8 uses much deeper and more complex architectures of neural networks. Other classifiers used in A8 are based on non-neural network-based machine learning. The array of non-deep learning-based machine learning classifiers used in A8 can also include XGboost based classifiers. A9 embodies an assemble method-based algorithm that takes the weighted average of the output of all the classifiers to minimize the false positive and false negative rate of the screening result. The weights are calculated based on the sensitivity of each classifier observed in the past as well as the based-on degree of independence they have from other classifiers. This degree of independence is calculated using a correlation between the training data used for the classifiers and the similarity between their architectures. A1 can then format the diagnosis results, fuses them with a-priory information if any, and feeds it back to the user. Training the Cough Detection and Diagnosis AI Engines A6 and A8:

These engines can be trained with a cough and other vocal sounds of subjects that are known to have COVID-19 infection as well as those who do not have COVID-19 infection. Additionally, a large variety of environmental sounds can also be used in training the AI engines in A6 and A8. One of the several breakthroughs that have enabled this invention is its ability to yield reliable diagnosis results even with a relatively small amount of training data from COVID-19 positive patients. To overcome cough and vocal sound training data shortage from the COVID-19 patients the invention can use transfer learning. Here a large variety of non-cough sounds, cough sounds, as well as image data is used to initialize the weights of certain layers of the deep learning-based AI engines in blocks A6 and A8. Additionally, in the pre-processing block A2, the invention uses generative adversarial networks and variational auto-encoders to overcome the training data sparsity problem.

Using machine learning on the user mobility and location data for the population along with the testing results at A10, the disclosed system can predict the risk of exposure for individuals at a certain location and time. The user mobility information can be obtained for past and in near rear time from an external server. This information can be shared with individuals via the interface. As the location is sensitive and private information, A11 is designed to work with anonymized location information. Also, being informed of potential exposure risks can act as an incentive to encourage users to allow location sharing. For users that do not allow location sharing e.g., via GPS, A11 estimates location via triangulation method by exploiting received signal strength from the cellular network or Wi-Fi hotspots. Thus, the individuals at risk of exposure can be informed by disclosed system through device carried or worn by the individuals.

The disclosed system can additionally predict a spatiotemporal live map of the spread. Given that continual and in-situ screening can be performed anytime anywhere, a proprietary algorithm in A11 aggregates the spatially and temporally stamped anonymized test results to create a live map of the infection spread. Where needed A11 can use matrix completion and kriging techniques to create a map from the sparse data. Moreover, the disclosed invention can also provide for prediction of the future hotspots and outbreak locations: A11 can also use results of A10 and fuses them with mobility patterns of the user from the past (obtained from CDR data, location, handover traces) and other publicly available information from external servers to predict future hotspots and locations of the outbreak. The method can use deep learning, XGboost, and Markov chain-based proprietary models. This model takes mobility patterns and the spatiotemporally tagged test results from A10 as input and returns future hotspots and outbreak locations as output.

Figure 6:
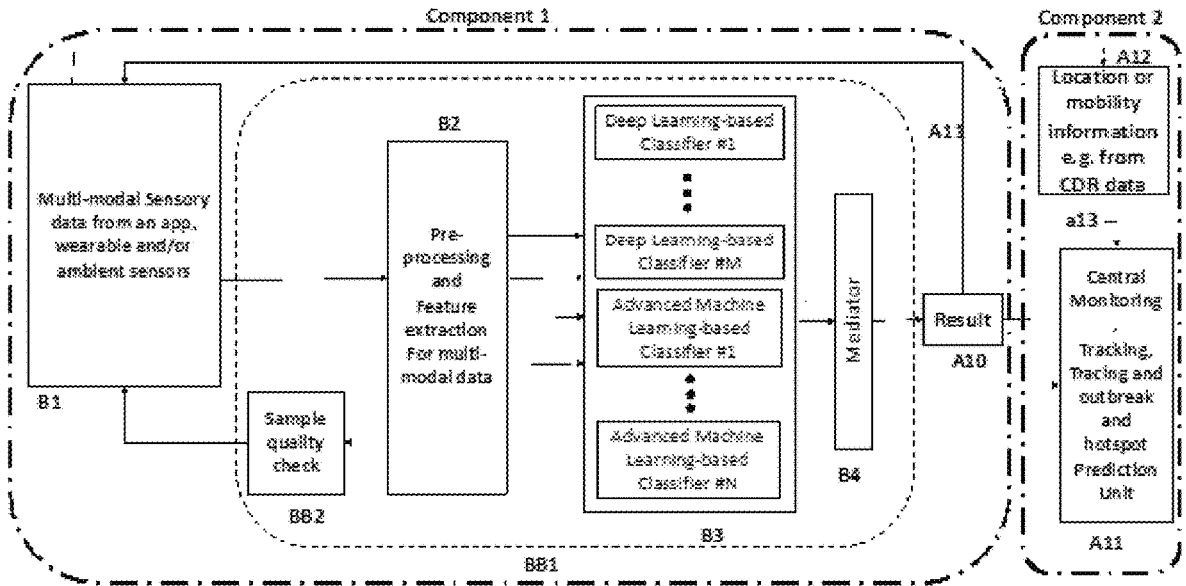
FIG. 6 is a block diagram showing an exemplary embodiment of the method for screening individuals for COVID-19 infection using multimodal sensor data, according to an exemplary embodiment of the present invention.

Referring to FIG. 6 which discloses an exemplary embodiment of the computer-implemented method for screening COVID-19 and other infection in individuals using multimodal sensory data. The multimodal sensory data may include recording of cough sound, breathing sound, vocalization of pre-defined words and sentences to gauge lung capacity and breathing difficulty; pictures/movies of face, hands, trunk, and feet and retina taken from phone or other devices; biomarkers including respiration rate, temperature, blood oxygen saturation, pulse rate, heart rate variability, resting heart rate, blood pressure, mean arterial pressure, stroke volume, sweat level, systematic vesicular resistance, cardiac output, pulse pressure, cardiac index, one lead ECG and breath chemical composition including volatile organic compounds; and metadata including Age, gender, smoking, non-smoking, ethnicity, and medical history.

The multimodal sensory data can be collected by B1 and passed on to B2. B1 can be manifested in form of a smartphone that is linked to wearable, carriable, or ambient sensors. Example wearable and carriable sensors include smartwatches, rings, necklaces, over the skin or under the skin patches, or carriable devices such as breath-meters. Ambient sensors include electromagnetic sensors (infra-red, visible light cameras or wireless sensors) or audio sensors, or biochemical sensors.

B1 can also be manifested as a custom device that is capable of either directly collecting the data or through connected wearable or ambient sensors. B2 here is a multimodal data pre-processing and feature extraction unit. B2 extracts distinct domain-aware features for each of the four types of data and passes it on to the B3 that has specific AI algorithms trained on each data stream, as well as deep learning and XGboost based models that take all data streams as input simultaneously. Together with B2 and B3 process the multimodal data to extract, augment and amplify latent features in data linked with COVID-19 infection to return screening results. These features include but are not limited to: Distinct latent features in cough and other human sounds associated with COVID-19 induced pathomorphological alternations in the human body; Cutaneous manifestations of COVID-19 infection in form of anomalies in the skin; Anomalies in one or more of the following biomarkers: Respiration rate, temperature, blood oxygen saturation, pulse rate, heart rate variability, resting heart rate, blood pressure, mean arterial pressure, stroke volume, sweat level, systematic vesicular resistance, cardiac output, pulse pressure, cardiac index, one lead ECG and breath chemical composition including volatile organic compounds; and Neurologic manifestations that include but are not limited to central nervous system manifestations (dizziness, headache, impaired consciousness, acute cerebrovascular disease, ataxia, and seizure), peripheral nervous system manifestations (taste impairment, smell impairment, vision impairment, and nerve pain), and skeletal muscle injury manifestations.

B4 deduces the final result by not only weighing the individual algorithm performance in B3, but also based on the data stream used. For example, if certain biomarkers are available, the result of the diagnostic engine using those biomarkers is given more weight compared to the diagnostic engine in B3 that detects an anomaly in the skin images. The weights between diagnoses achieved from different data streams are determined using a combination of performance on past test and training data as well as domain knowledge from the medical field. For example, compared to only 20% covid-19 patients showing cutaneous symptoms 75% show cough as a symptom, 70% show fever as a symptom. These priors are exploited by the mediator B4 using Bayesian analysis to determine the final result. The rest of the blocks in Embodiment 2 have the same functionality as described for Embodiment 1.

It is to be understood that certain embodiments have been described with reference to COVID-19 screening, however, the disclosed invention can be used to screen any other microbial infection that affects the respiratory system, and thus the respiratory sounds. Such diseases can include SARS, MERS, COVID-19, Influenza; Corona Virus infections; Upper respiratory tract infections (mostly viral); Lower respiratory tract infections (e.g., pneumonia, bronchitis, bronchiolitis); Upper airway cough syndrome; Pertussis, parapertussis; Tuberculosis; Asthma and allergies; Chronic obstructive pulmonary disease (emphysema, chronic bronchitis); Postnasal drip, Croup, Laryngitis, Tracheitis; Lung abscess; Trachea, Bronchus, Lung cancers, smoking; Pleural diseases; Pneumoconiosis, Early interstitial fibrosis, cystic fibrosis; Pulmonary embolism; Trachesophageal fistula; New communicable diseases that may present similar symptoms across the population in terms of latent features within cough, human sounds, skin images, and other biomarkers and meta data collected by the invention; Oral cancer, diabetes mellitus, Renal diseases, cirrhosis; Ischemic Heart Disease, Stroke, Left-ventricular failure, Congestive heart failure (pulmonary edema); Thyroid Cooper, Hypothyroidism, (enlarged) thyroid hypertrophy; Laryngopharyngeal reflux; Somatic cough syndrome; Vocal cord dysfunction; Obstructive sleep apnea; Psychogenic cough/Idiopathic cough; Depression, Anxiety, Schizophrenia; Gastro-esophageal reflux; Mediastinal tumor; Arnold nerve ear-cough reflex; Alzheimer Disease and other Dementias; and Colon and rectum cancers.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A method for predicting a likelihood of having a respiratory infection in an individual, hotspot breakout prediction, spatiotemporal monitoring of spread, and community-level resolution, the method implemented within a screening system, the screening system having a processor and a memory, the method comprising:

receiving, by the screening system, cough sound samples from subjects suffering from the respiratory infection and subjects not suffering from the respiratory infection;

applying temporal and spectral pre-processing techniques to the cough sound samples for removing noise, wherein the temporal and spectral pre-processing techniques comprises amplitude normalization, audio segmentation, frequency-selective filtering, and pitch shifting;

pre-processing the cough sound samples, by a pre-processing module implemented within the screening system, into labeled features obtaining a training dataset;

randomly partitioning the training dataset into a plurality of training datasets;

generating a plurality of classifiers, by the screening system using machine learning, based on the plurality of training datasets, wherein at least one classifier of the plurality of classifiers is a deep learning classifier; and assigning a weightage, by the screening system, to each classifier of the plurality of classifiers, the weightage is assigned to each classifier based on a parameter of a plurality of parameters used for generating each classifier, wherein the plurality of parameters are selected from a group consisting of biomarkers, metadata, neurologic manifestations including central nervous system manifestations and peripheral nervous system manifestations, and images of cutaneous manifestations of the respiratory infection in a form of anomalies in skin;

computing, by a mediator module implemented within the system an average weightage of a plurality of outputs from the plurality of classifiers, based on the weightage assigned to each classifier of the plurality of classifiers to obtain a result, the plurality of outputs are obtained via processing a set of unique latent features of the cough sound samples by the plurality of classifiers, wherein the result classifies the individual into a category indicative of the likelihood of having the respiratory infection or into another category indicative of the likelihood of not having the respiratory infection, and;

communicating, by the mediator module, the result to the individual.

2. The method according to claim 1, wherein the method further comprises:

receiving, by the screening system, a sound sample from the individual, the sound sample includes a cough sound;

applying the temporal and spectral pre-processing techniques to the sound sample for removing noise;

extracting the set of unique latent features from the sound sample, using a feature extraction algorithm, wherein the feature extraction algorithm is based on audio acoustics and medical domain knowledge;

determining variants, sub-components, and combinations of the set of unique latent features using the medical domain knowledge;

maximizing entropy and reducing dimensions of input feature vectors;

performing algebraic operations and transformations on the variants, sub-components, and combinations of the set of unique latent features; and processing the variants, sub-components, and combinations of the set of unique latent features by each of the plurality of classifiers to obtain the plurality of outputs, each output of the plurality of outputs indicates the likelihood of having the respiratory infection or the likelihood of not having the respiratory infection.

3. The method according to claim 2, wherein the method further comprises:

receiving the plurality of sound samples from the plurality of individuals;

computing the plurality of results for the plurality of individuals by processing the plurality of sound samples;

receiving a plurality of location coordinates of the plurality of individuals;

applying machine learning algorithms to the plurality of results of the plurality of individuals and the plurality of location coordinates for presenting in near real time rate and pattern of a spread of the respiratory infection as analysis;

presenting the analysis as an overlay on a spatiotemporal live map showing continuous near real time spread of infection; and graphically presenting predicted future hotspots.

4. The method according to claim 3, wherein the method further comprises:

predicting, by the screening system, cluster spreads of the respiratory infection in a near future; and graphically presenting the cluster spread.

5. The method according to claim 4, wherein the method further comprises receiving past mobility patterns of the plurality of individuals from an external server, wherein the predicting of the future hotspots and cluster spreads is further based upon the past mobility patterns.

6. The method according to claim 1, wherein the method further comprises:

installing, the pre-processing module and the plurality of classifiers into a user device, the user device comprises a processor and a memory;

receiving a sound sample from the individual-through a microphone coupled to the user device, the sound sample includes a cough sound;

pre-processing the sound sample, by the pre-processing module on the user device, to remove noise and extract the set of unique latent features;

processing the set of unique latent features by each of the plurality of classifiers, on the user device, to obtain the plurality of outputs, each output of the plurality of outputs indicates the likelihood of having the respiratory infection or the likelihood of not having the respiratory infection;

computing, by the user device, the average weightage of the plurality of outputs based on the weightage assigned to each classifier of the plurality of classifiers to obtain the result, wherein the result classifies the individual into a category indicative of the likelihood of having the respiratory infection or into another category indicative of the likelihood of not having the respiratory infection; and presenting the result on a display coupled to the user device.

7. The method according to claim 1, wherein the respiratory infection is selected from a group consisting of COVID-19 infection, SARS, MERS, influenza, upper respiratory tract infections, lower respiratory tract infections, upper airway cough syndrome, pertussis, parapertussis, tuberculosis, asthma, chronic obstructive pulmonary disease, laryngitis, lung cancers, pneumoconiosis, corona virus infections, pneumonia, bronchitis, emphysema, chronic bronchitis, postnasal drip, croup, tracheitis, lung abscess, trachea cancer, bronchus cancer, smoking, pleural diseases, pneumoconiosis, early interstitial fibrosis, cystic fibrosis, pulmonary embolism, trach-esophageal fistula, laryngopharyngeal reflux, somatic cough syndrome, vocal cord dysfunction, obstructive sleep apnea, psychogenic cough/idiopathic cough, mediastinal tumor, arnold nerve ear-cough reflex, alzheimer disease, dementias, colon cancer, and rectum cancer.

8. The method according to claim 1, wherein the method further comprises:

pre-processing the plurality of parameters to obtain a plurality of additional training datasets, wherein the generating of the plurality of classifiers is further based on the plurality of additional training datasets.

9. The method according to claim 1, wherein the biomarkers are selected from a group consisting of respiration rate, body temperature, blood oxygen saturation, pulse rate, heart rate variability, resting heart rate, blood pressure, mean arterial pressure, stroke volume, sweat level, systematic vesicular resistance, cardiac output, pulse pressure, cardiac index, one lead ECG, and breath chemical composition including volatile organic compounds.

10. The method according to claim 1, wherein the metadata is selected from a group consisting of age, gender, smoking, non-smoking, ethnicity, and medical history.

11. The method according to claim 1, wherein the central nervous system manifestations are selected from a group consisting of dizziness, headache, impaired consciousness, acute cerebrovascular disease, ataxia, and seizure, and the peripheral nervous system manifestations are selected from a group consisting of taste impairment, smell impairment, vision impairment, and nerve pain.

12. A method for predicting a likelihood of having a respiratory infection in an individual, the method implemented within a screening system, the screening system has a processor and a memory, the method comprising:

receiving, by the screening system, a sound sample from the individual, the sound sample includes a cough sound, nasal breathing sounds, and vocalization sounds;

pre-processing the sound sample, by a pre-processing module, to remove noise and extract a set of unique latent features, the pre-processing module implemented within the screening system;

processing the set of unique latent features by a plurality of machine learning based classifiers;

computing, by a mediator module implemented within the system an average weightage of a plurality of outputs from the plurality of classifiers, based on the weightage assigned to each classifier of the plurality of classifiers to obtain a result, the plurality of outputs are obtained via processing the set of unique latent features of the sound samples by the plurality of classifiers, based on the result classifying the individual into a category indicative of the likelihood of having the respiratory infection or into another category indicative of a likelihood of not having the respiratory infection, wherein each classifier is configured to classify the individual into the two categories, wherein each classifier is assigned a weightage; the weightage is assigned to each classifier based on a parameter of a plurality of parameters used for generating each classifier, wherein the plurality of parameters are selected from a group consisting of biomarkers, metadata, neurologic manifestations including central nervous system manifestations and peripheral nervous system manifestations, and images of cutaneous manifestations of the respiratory infection in a form of anomalies in skin; and communicating, by the mediator module, the result to the individual.

13. The method according to claim 12, wherein the respiratory infection is selected from a group consisting of COVID-19 infection SARS, MERS, influenza, upper respiratory tract infections, lower respiratory tract infections, upper airway cough syndrome, pertussis, parapertussis, tuberculosis, asthma, chronic obstructive pulmonary disease, laryngitis, lung cancers, pneumoconiosis, corona virus infections, pneumonia, bronchitis, emphysema, chronic bronchitis, postnasal drip, croup, tracheitis, lung abscess, trachea cancer, pleural diseases, pneumoconiosis, early interstitial fibrosis, cystic fibrosis, pulmonary embolism, trach-esophageal fistula, laryngopharyngeal reflux, somatic cough syndrome, vocal cord dysfunction, obstructive sleep apnea, psychogenic cough/idiopathic cough, arnold nerve ear-cough reflex.

14. The method according to claim 12, wherein the plurality of machine learning based classifiers comprises a deep transfer learning-based binary classifier.

15. A screening system for predicting a likelihood of having a disease in an individual, the disease effecting respiratory sounds, the screening system having a processor and a memory, the system configured to implement a method comprising:

receiving, by the screening system, cough sound samples from subjects suffering from the disease and subjects not suffering from the disease;

pre-processing the cough samples, by a pre-processing module implemented within the screening system, into labeled features obtaining a training dataset;

randomly partitioning the training dataset into a plurality of training datasets;

generating a plurality of classifiers, by the screening system using machine learning, based on the plurality of training datasets, wherein at least one classifier of the plurality of classifiers is a deep learning classifier;

assigning a weightage, by the screening system, to each classifier of the plurality of classifiers, the weightage is assigned to each classifier based on a parameter of a plurality of parameters used for generating each classifier, wherein the plurality of parameters are selected from a group consisting of biomarkers, metadata, neurologic manifestations including central nervous system manifestations and peripheral nervous system manifestations, and images of cutaneous manifestations of the respiratory infection in a form of anomalies in skin;

computing, by a mediator module implemented within the system an average weightage of a plurality of outputs from the plurality of classifiers, based on the weightage assigned to each classifier of the plurality of classifiers to obtain a result, the plurality of outputs are obtained via processing a set of unique latent features of the sound samples by the plurality of classifiers, wherein the result classifies the individual into a category indicative of the likelihood of having the disease or into another category indicative of the likelihood of not having the disease, wherein each classifier is configured to distinguish the individual into one of the two categories, the categories being positive and negative;

communicating, by the mediator module, the result to the individual.

16. The system according to claim 15, wherein the method further comprises:

receiving, by the screening system, a sound sample from the individual, the sound sample includes a cough sound; and pre-processing the sound sample, by the pre-processing module, to remove noise and extract a set of unique latent features.

17. The system according to claim 15, wherein the disease is selected from a group consisting of COVID-19 infection, SARS, MERS, influenza, upper respiratory tract infections, lower respiratory tract infections, upper airway cough syndrome, pertussis, parapertussis, tuberculosis, asthma, chronic obstructive pulmonary disease, laryngitis, lung cancers, pneumoconiosis, corona virus infections, pneumonia, bronchitis, emphysema, chronic bronchitis, postnasal drip, croup, tracheitis, lung abscess, trachea cancer, bronchus cancer, smoking, pleural diseases, pneumoconiosis, early interstitial fibrosis, cystic fibrosis, pulmonary embolism, trach-esophageal fistula, laryngopharyngeal reflux, somatic cough syndrome, vocal cord dysfunction, obstructive sleep apnea, psychogenic cough/idiopathic cough, mediastinal tumor, arnold nerve ear-cough reflex, alzheimer disease, dementias, colon cancer, and rectum cancer.

\* \* \* \* \*